(12) United States Patent
Jones

(10) Patent No.: US 10,702,365 B2
(45) Date of Patent: Jul. 7, 2020

(54) METHOD AND APPARATUS FOR UTILIZING MESH TEMPLATES

(71) Applicant: Frank K. Jones, Atlanta, GA (US)

(72) Inventor: Frank K. Jones, Atlanta, GA (US)

( * ) Notice: Subject to any disclaimer, the term of this patent is extended or adjusted under 35 U.S.C. 154(b) by 225 days.

(21) Appl. No.: 15/228,275

(22) Filed: Aug. 4, 2016

(65) Prior Publication Data

US 2017/0035543 A1  Feb. 9, 2017

Related U.S. Application Data

(60) Provisional application No. 62/201,306, filed on Aug. 5, 2015.

(51) Int. Cl.
*A61F 2/00* (2006.01)

(52) U.S. Cl.
CPC .... *A61F 2/0063* (2013.01); *A61F 2250/0097* (2013.01)

(58) Field of Classification Search
CPC ............. A61F 2/0063; A61F 2240/005; A61F 2250/0097; Y10T 428/15
See application file for complete search history.

(56) References Cited

U.S. PATENT DOCUMENTS

| | | | | |
|---|---|---|---|---|
| 2005/0085924 A1* | 4/2005 | Darois | .................. | A61F 2/0063 623/23.74 |
| 2005/0288691 A1* | 12/2005 | Leiboff | .................. | A61F 2/0063 606/151 |
| 2007/0123915 A1* | 5/2007 | Kammerer | ............ | A61F 2/0045 606/151 |
| 2008/0167729 A1* | 7/2008 | Nelson | .................. | A61F 2/0063 623/23.72 |
| 2010/0312043 A1* | 12/2010 | Goddard | ............... | A61F 2/0045 600/30 |
| 2011/0306989 A1* | 12/2011 | Darois | ............... | A61B 17/0057 606/144 |
| 2014/0094829 A1* | 4/2014 | Kostrzewski | ......... | A61F 2/0063 606/151 |

* cited by examiner

*Primary Examiner* — Thomas M McEvoy

(57) ABSTRACT

This disclosure relates generally to repair of defective hernias by use of a mesh material. However, inaccurate hernia defect measurements can cause ineffective treatment and a waste of mesh material. Therefore, accurate hernia defect measurements can aid in the effective treatment and repair of hernia defects.

19 Claims, 6 Drawing Sheets

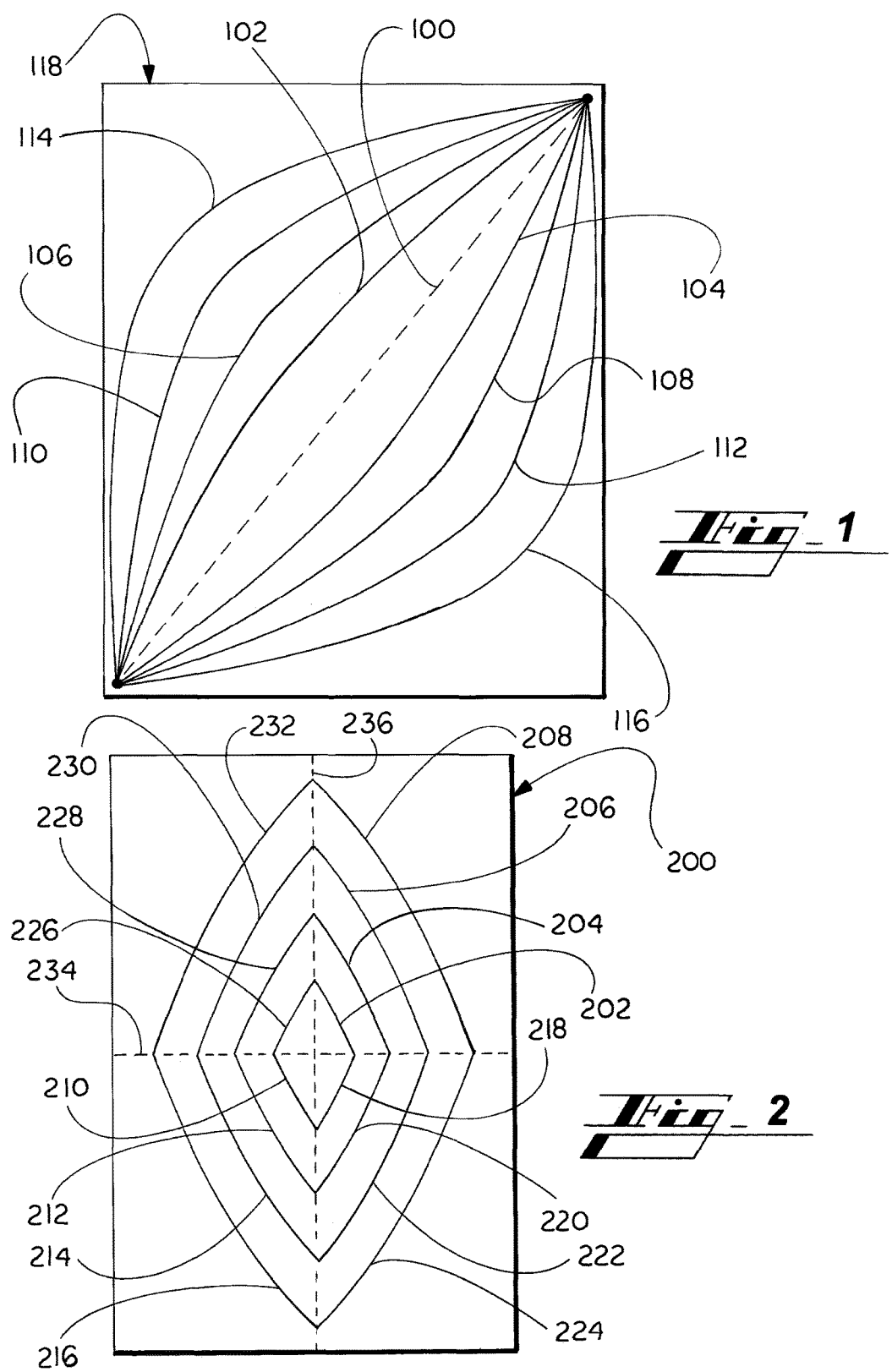

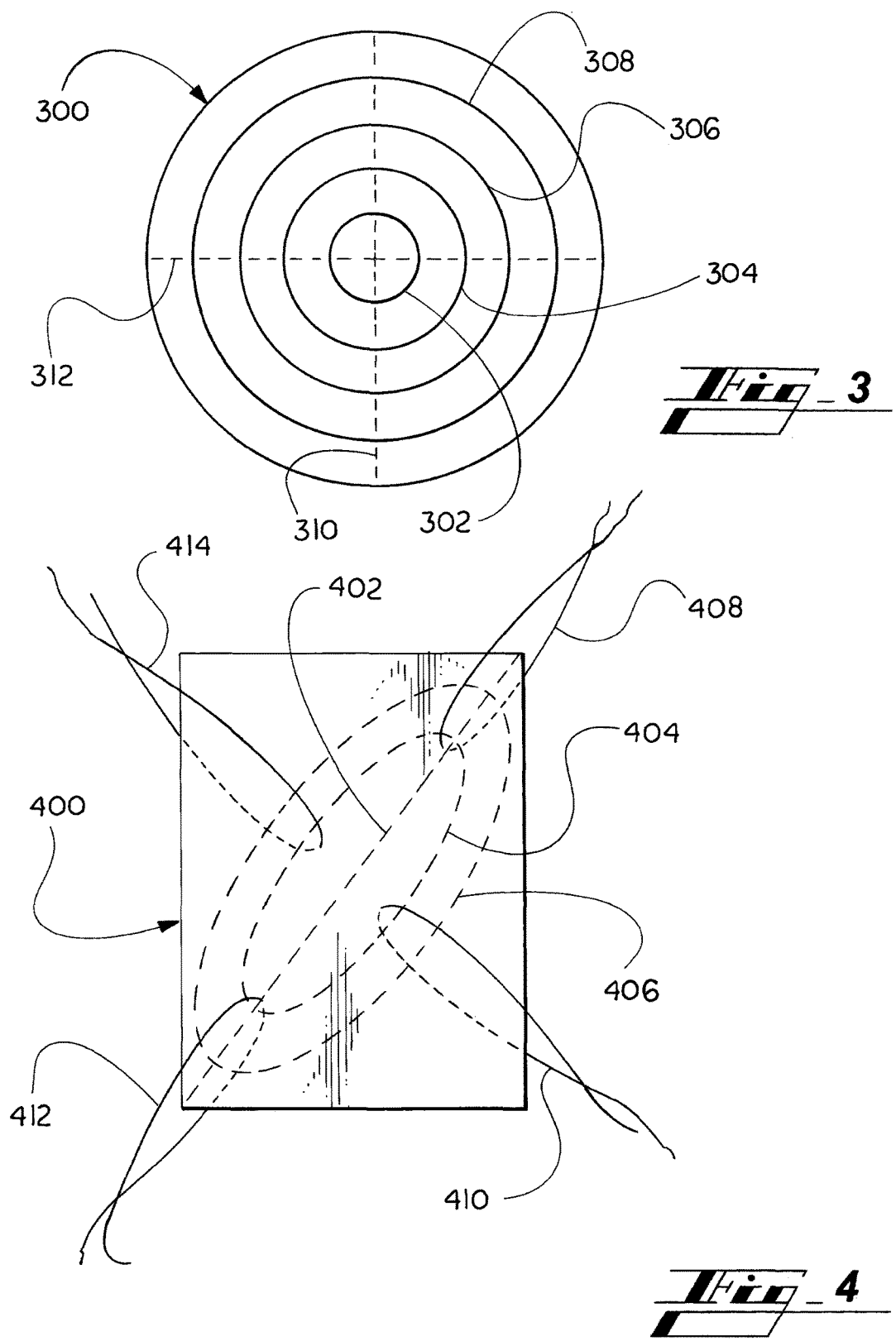

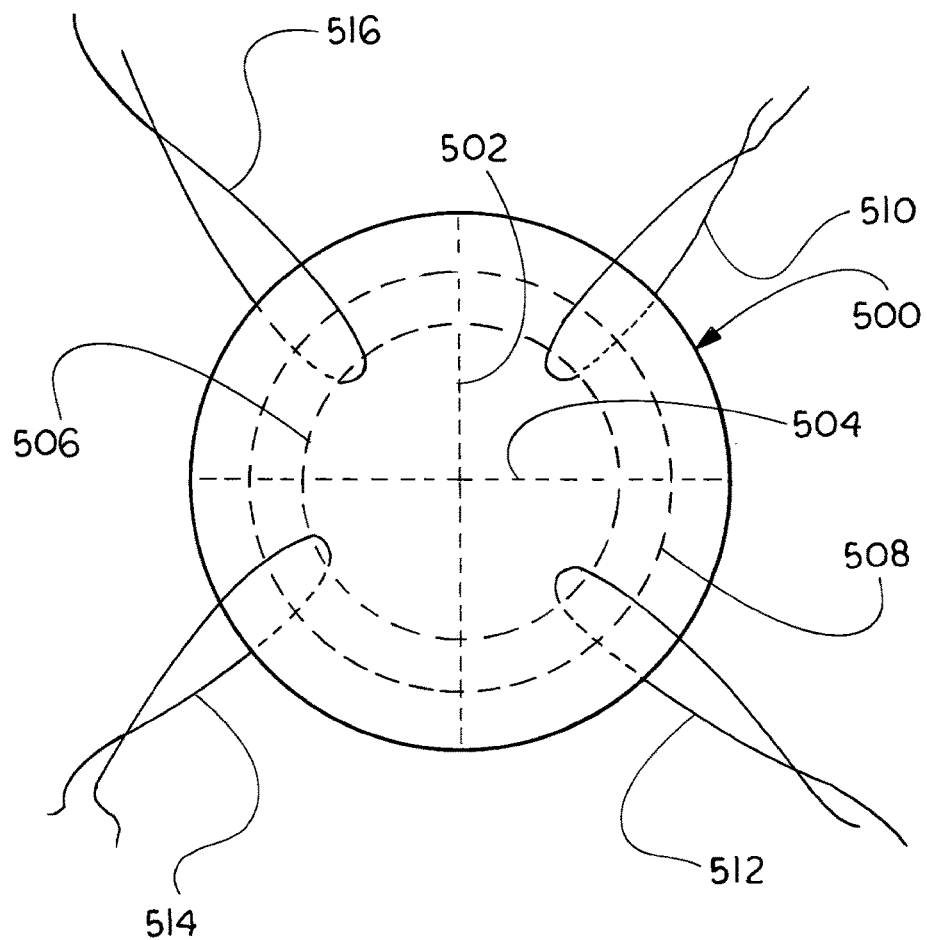
Fig_5

METHOD AND APPARATUS FOR UTILIZING MESH TEMPLATES

CROSS REFERENCE TO RELATED APPLICATION

This application claims priority to U.S. Provisional Patent Application No. 62/201,306, filed on Aug. 5, 2015, and entitled "METHOD AND APPARATUS FOR UTILIZING MESH TEMPLATES," the entirety of which is hereby incorporated herein by reference.

TECHNICAL FIELD

This disclosure relates generally to the use of mesh templates. More specifically, this disclosure relates to the use of mesh templates to facilitate surgical procedures.

BACKGROUND

Surgical mesh is a loosely woven sheet, which is used as either a permanent or temporary support for organs and other tissues during surgery. The meshes are available in both inorganic and biological materials, and are used in a variety of surgeries. Though hernia repair surgery is the most common application, they can also be used for reconstructive work, such as in pelvic organ prolapse.

Permanent meshes can remain in the body, whereas temporary meshes dissolve over time. Some meshes combine permanent and temporary meshes such as Vipro; a brand name for a product combining the re-absorbable material vipryl, made from polyglycolic acid, and prolene, a non-reabsorbable polypropylene.

The above-described background relating to mesh size and placement is merely intended to provide a contextual overview of some current technology, and is not intended to be exhaustive. Other context regarding the state of the art may become further apparent upon review of the following detailed description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the purpose of this summary is to present some concepts related to some exemplary non-limiting embodiments in simplified form as a prelude to more detailed descriptions of the various embodiments that follow in the disclosure.

Accurate hernia measurement can be used to determine the proper size mesh to apply and ultimately reduce material costs. A hernia measurement apparatus can assist a surgeon in choosing the correct size mesh to repair a defect. Opening meshes that are not the correct size for a procedure can generate additional costs for hospitals and patients. Thus, there can be a significant cost increase if the wrong size mesh is chosen. Therefore it is important to have accurate measurements for hernia defects. Currently surgeons are using arbitrary measurements or educated guesses to make their decisions. A hernia measurement apparatus can help the surgeon standardize and more accurately measure fascial defect sizes, thereby allowing the surgeon to choose a correct size mesh for the repair. A mesh measurement template can measure hernia defects more accurately and consistently, thereby allowing the appropriate mesh size to be selected.

A mesh template can be used to help a surgeon to accurately measure a fascial defect. The mesh template can help the surgeon draw the dimensions of the hernia defect directly onto the mesh to allow the surgeon to shape and cut away excess mesh; it can help with the ease, accuracy, and efficiency of placement; and/or it can be used with an open or laparoscopic technique. The mesh template can be made from a variety of different materials including, but not limited to: plastic, silastic, durable (nonabsorbent) paper, metal, and/or metalloid products such as steel, aluminum, or tin. If metal is used, it can be flexible and can have the ability to be sterilized. The mesh template can be transparent and can also comprise an attachment or prong in a position, which is adjacent to the mesh template to facilitate placement of the mesh template while it is being used. For example, the attachment could be perpendicular to the mesh template face but it could also be placed at a variety of other angles.

The mesh template can also comprise several different shapes to more accurately represent several different shaped fascial defects. For instance, the mesh template can include, but is not limited to: round shaped designs, oval shaped designs, diamond shaped designs, etc. It should be noted that a round shaped mesh template can be applied to a round shaped fascial defect, an oval shaped mesh template can be applied to an oval shaped fascial defect, and so on.

Furthermore, the mesh template can comprise a geometric representation of the fascial defects and references letters or numbers to indicate representative spacing. For instance, reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc.

The mesh template can also comprise perforations at one or more reference lines, which can facilitate one template being able to be utilized for several sized fascial defects. Each perforated shape/design can also be highlighted to provide visibility for each specific shape/design. In an alternate embodiment, the different shapes can be represented by different lines and/or perforations on each side of the template. For example, one side of the mesh template can comprise a geometric shape, reference numerals, and perforations representative of an oval shaped design, whereas the opposing side of the mesh template can comprise a geometric shape, reference numerals, and perforations representative of a diamond shaped design. The aforementioned embodiment can allow a surgeon to select from an oval shaped design or a diamond shaped design while repairing a fascial defect. This can allow for flexibility during surgical procedures and reduced production costs for mesh templates.

Combining a mesh with a suture can create efficiencies in the surgical process by reducing time. A mesh-suture combination can have several sutures that have already been strategically placed on the mesh during processing. In other words, when the mesh is removed from a sterile packaging, the mesh can already have strategically pre-placed sutures attached or embedded. There can be a complete set of sutures surrounding the entire mesh, which will require a surgeon to already know the dimensions of the hernia defect and the size of the mesh that he wants to use to repair the defect.

The mesh can comprise any currently commercially available meshes, both biologic and synthetic. The mesh can be composed of biological tissues, including, but not limited to: human, porcine, bovine, pericardium, intestine, etc. The mesh can also be composed of synthetic materials including, but not limited to: polypropylene, polyester, polytetrafluoroethylene, etc. The mesh can also comprise a combination of both biological and synthetic-based materials. The mesh could also be pre-shaped into specific geometric shapes, which can comprise pre-located sutures.

The pre-located sutures can be placed circumferentially around the mesh at a defined distance from each other. For instance, each pre-located suture could be placed two centimeters apart. For an oval and a diamond shape mesh there can be a suture pre-located within each vertex. Using the mesh template, a surgeon can determine the size of mesh, comprising pre-located sutures, which he/she will need to utilize for the fascial overlap to repair a hernia.

The pre-located suture placement patterns can mirror known hernia defect boundaries. For instance, the suture locations for ventral hernias can include, but is not limited to: 1) towards the north corner of the mesh (superior apex of the defect) four centimeters from the corner, 2) towards the south corner of the mesh (inferior apex of the defect) four centimeters from the corner; 3) towards the east corner of the mesh (lateral aspect of the defect) four centimeters from the corner; and/or towards the west corner of the mesh (lateral aspect of the defect) four centimeters from the corner. When the mesh template is placed in an abdominal cavity, the mesh template can be turned so that there is a diamond configuration. For umbilical hernias, the sutures can be place at pre-determined intervals in a circumferential manner. The sutures can also be removed from the mesh and repositioned according to the surgeon's desired location of the stitch. Additional embodiments can include, but are not limited to changing the location and/or the number of the sutures.

Advantages of mesh-suture combination include, but are not limited to: 1) the sutures can help in securing the mesh to a patient's abdominal wall; 2) it can decrease the fixation time of the mesh to the abdominal wall; 3) it can allow for more consistent placement of the sutures, therefore providing for a better closure; and/or 4) it can decrease the overall time of the repair.

Described herein are systems, articles of manufacture, and other embodiments or implementations that can facilitate the use of a mesh and mesh template to stitch a mesh to a fascial defect.

According to one embodiment, described herein is an apparatus for facilitating accurate measurement of fascial defects. The apparatus can comprise reference lines in relation to a shape of a mesh template. The apparatus can also comprise numbers representing distances in relation to the reference lines and a perforated shape, wherein the perforated shape is in accordance with the shape of the mesh template.

According to another embodiment, described herein is a method for facilitating accurate measurement of fascial defects. The method can comprise selecting a mesh template according to a perceived shape of a hernia and aligning the mesh template with a hernia. Furthermore, the method can comprise identifying numbers, on the mesh template, representing distances in relation to the hernia resulting in identified numbers, and selecting a mesh based on the perceived shape of the hernia and the identified numbers on the hernia mesh.

According to yet another embodiment, described herein is an apparatus for facilitating accurate measurement of fascial defects. The apparatus can comprise a symmetrical shape, wherein similar smaller symmetrical shapes are outlined by perforations, a label representing a distance associated with the similar smaller symmetrical shapes, and a prong adjacently attached to the mesh template.

These and other embodiments or implementations are described in more detail below with reference to the drawings.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

FIG. 1 illustrates an example fascial defect mesh template to measure the size of a fascial defect.

FIG. 2 illustrates an example diamond shaped mesh template to measure the size of a fascial defect.

FIG. 3 illustrates an example ventral hernia mesh template.

FIG. 4 illustrates an example mesh with pre-located sutures.

FIG. 5 illustrates an example ventral hernia mesh template comprising pre-located sutures.

DETAILED DESCRIPTION

Figure 6:
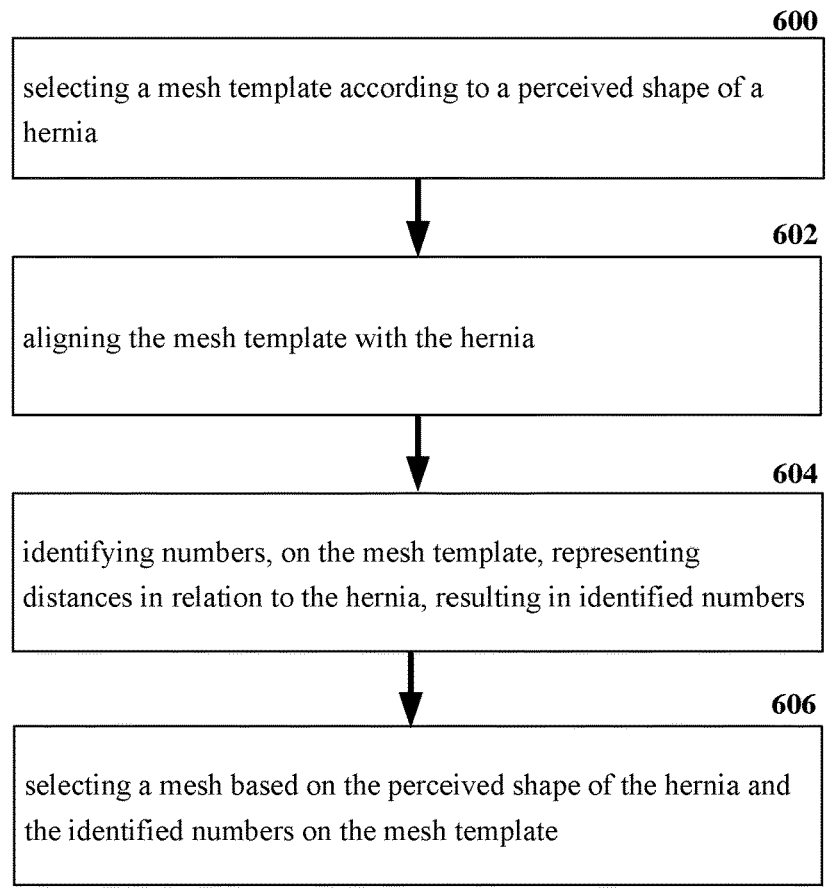
FIG. 6 illustrates is an example system block diagram for a method of using a mesh template apparatus.

In the following description, numerous specific details are set forth to provide a thorough understanding of various embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment," or "an embodiment," means that a particular feature, structure, or characteristic described in connection with the embodiment is included in at least one embodiment. Thus, the appearances of the phrase "in one embodiment," "in one aspect," or "in an embodiment," in various places throughout this specification are not necessarily all referring to the same embodiment. Furthermore, the particular features, structures, or characteristics may be combined in any suitable manner in one or more embodiments.

The words "exemplary" and/or "demonstrative" are used herein to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

As an overview of the various embodiments presented herein, to correct for the above identified deficiencies and other drawbacks of measuring fascial defects, various embodiments are described herein to facilitate the accurate measurement and repair of fascial defects.

For simplicity of explanation, the methods (or algorithms) are depicted and described as a series of acts. It is to be understood and appreciated that the various embodiments are not limited by the acts illustrated and/or by the order of acts. For example, acts can occur in various orders and/or concurrently, and with other acts not presented or described herein. Furthermore, not all illustrated acts may be required to implement the methods. In addition, the methods could alternatively be represented as a series of interrelated states via a state diagram or events. Additionally, the methods described hereafter are capable of being stored on an article of manufacture (e.g., a computer readable storage medium) to facilitate transporting and transferring such methodologies to computers. The term article of manufacture, as used herein, is intended to encompass a computer program accessible from any computer-readable device, carrier, or media, including a non-transitory computer readable storage medium.

Referring now to FIG. 1, illustrated is an example fascial defect mesh template to measure the size of a fascial defect. The mesh template can comprise equidistant reference lines in relation to a midpoint according to a shape of the mesh template. Reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc. Thus, the mesh template can comprise numbers representing distances in relation to the reference lines spaced equidistantly from a midpoint of the mesh template. Furthermore, the mesh template can comprise a perforated shape, wherein the perforated shape is in accordance with the shape of the mesh template The mesh template can comprise perforations at one or more reference lines, which can facilitate one template being able to be utilized for several sized fascial defects. Each perforated shape/design can also be highlighted to provide visibility for each specific shape/design.

The mesh template 118 can comprise biological and/or synthetic materials. The geometry of the mesh template 118 can be oval shaped based on a center line 100. From the center line 100 there can be lines 102, 104, 106, 108, 110, 112, 114, 116 which are equidistant from the center line 100. The lines 102, 104, 106, 108, 110, 112, 114, 116 can comprise similar shapes, which are smaller versions of the entire oval shape. For instance, using center line 100 as a start point, lines 102 104 create a similar, but smaller, oval shape to that of lines 106, 108. The lines 102, 104, 106, 108, 110, 112 114, 116 can also be perforated.

Referring now to FIG. 2, illustrated is an example diamond shaped mesh template to measure the size of a fascial defect. The mesh template can comprise equidistant reference lines in relation to a midpoint according to a shape of the mesh template. Reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc. Thus, the mesh template can comprise numbers representing distances in relation to the reference lines spaced equidistantly from a midpoint of the mesh template. Furthermore, the mesh template can comprise a perforated shape, wherein the perforated shape is in accordance with the shape of the mesh template The mesh template can comprise perforations at one or more reference lines, which can facilitate one template being able to be utilized for several sized fascial defects. Each perforated shape/design can also be highlighted to provide visibility for each specific shape/design.

The mesh template can comprise a symmetrical shape, wherein similar smaller symmetrical shapes are outlined by perforations. The mesh template can comprise a geometric representation of the fascial defects and references letters or numbers to indicate representative spacing. The reference lines can be standard measured lines in numbered increments representing similar shapes within the mesh template. The mesh template can also comprise perforations at one or more reference lines, which can facilitate one template being able to be utilized for several sized fascial defects. Each perforated shape/design can also be highlighted to provide visibility for each specific shape/design. The mesh template can comprise a label representing a distance associated with the similar smaller symmetrical shapes, and a prong adjacently attached to the mesh template.

The mesh template 200 can comprise biological and/or synthetic materials. The geometry of the mesh template 200 can be diamond shaped based on center lines 234, 236. From the center lines 234, 236 there can be lines 202, 204, 206, 208, 210, 212, 214, 216, 218, 220, 222, 224, 226, 228, 230, 232, which are equidistant from the center lines 234, 236. The lines 202, 204, 206, 208, 210, 212, 214, 216, 218, 220, 222, 224, 226, 228, 230, 232 can comprise similar shapes, which are smaller versions of the entire diamond shape. For instance, using center lines 234, 236 as a start point, lines 202, 226, 210, 218 create a similar, but smaller, diamond shape to that of lines 232, 208, 224, 216. The lines 202, 204, 206, 208, 210, 212, 214, 216, 218, 220, 222, 224, 226, 228, 230, 232 can also be perforated.

The mesh template can comprise a symmetrical shape, wherein similar smaller symmetrical shapes are outlined by perforations. The mesh template can comprise a geometric representation of the fascial defects and references letters or numbers to indicate representative spacing. The reference lines can be standard measured lines in numbered increments representing similar shapes within the mesh template. The mesh template can also comprise perforations at one or more reference lines, which can facilitate one template being able to be utilized for several sized fascial defects. Each perforated shape/design can also be highlighted to provide visibility for each specific shape/design. The mesh template can comprise a label representing a distance associated with the similar smaller symmetrical shapes, and a prong adjacently attached to the mesh template.

Referring now to FIG. 3, illustrated is an example ventral hernia mesh template. The mesh template can comprise equidistant reference lines in relation to a midpoint according to a shape of the mesh template. Reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc. Thus, the mesh template can comprise numbers representing distances in relation to the reference lines spaced equidistantly from a midpoint of the mesh template. Furthermore, the mesh template can comprise a perforated shape, wherein the perforated shape is in accordance with the shape of the mesh template The mesh template can comprise perforations at one or more reference lines, which can facilitate one template being able to be utilized for several sized fascial defects. Each perforated shape/design can also be highlighted to provide visibility for each specific shape/design.

The mesh template can comprise a symmetrical shape, wherein similar smaller symmetrical shapes are outlined by perforations. The mesh template can comprise a geometric representation of the fascial defects and references letters or numbers to indicate representative spacing. The reference lines can be standard measured lines in numbered increments representing similar shapes within the mesh template. The mesh template can also comprise perforations at one or more reference lines, which can facilitate one template being able to be utilized for several sized fascial defects. Each perforated shape/design can also be highlighted to provide visibility for each specific shape/design. The mesh template can comprise a label representing a distance associated with the similar smaller symmetrical shapes, and a prong adjacently attached to the mesh template.

The mesh template 300 can comprise biological and/or synthetic materials. The geometry of the mesh template 300 can be circular based on center lines 310, 312. From the center lines 310, 312 there can be circles 302, 304, 306, 308 which are equidistant from the center lines 310, 312. The circles 302, 304, 306, 308 can comprise similar shapes, which are smaller versions of the entire circle shape. For instance, using center lines 310, 312 as a start point, circle 302 can be a similar, but smaller, circle to circle 306. The circles 302, 304, 306, 308 can also be perforated.

FIG. 4 illustrates an example mesh template with pre-located sutures. The mesh template can comprise equidistant reference lines in relation to a midpoint according to a shape of the mesh template. Reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc. Thus, the mesh template can comprise numbers representing distances in relation to the reference lines spaced equidistantly from a midpoint of the mesh template. Furthermore, the mesh template can comprise a perforated shape, wherein the perforated shape is in accordance with the shape of the mesh template The mesh template can comprise perforations at one or more reference lines, which can facilitate one template being able to be utilized for several sized fascial defects. Each perforated shape/design can also be highlighted to provide visibility for each specific shape/design.

The mesh template can comprise a symmetrical shape, wherein similar smaller symmetrical shapes are outlined by perforations. The mesh template can comprise a geometric representation of the fascial defects and references letters or numbers to indicate representative spacing. The reference lines can be standard measured lines in numbered increments representing similar shapes within the mesh template. The mesh template can also comprise perforations at one or more reference lines, which can facilitate one template being able to be utilized for several sized fascial defects. Each perforated shape/design can also be highlighted to provide visibility for each specific shape/design. The mesh template can comprise a label representing a distance associated with the similar smaller symmetrical shapes, and a prong adjacently attached to the mesh template.

The strategic locations of the sutures can form several patterns, including but not limited to: diamond, ellipse, and/or circular type patterns depending on what type of hernia is being repaired. The mesh template 400 can comprise a center line 402 with perforated ellipse shapes 404, 406. The mesh template 400 can also comprise pre-located sutures 408, 410, 412, 414. Therefore, if a surgeon uses the mesh template 400 to measure an ellipse shaped fascial defect, and the size of the fascial defect is close to that of ellipse shape 404, then the surgeon can remove the ellipse shape 404 from the mesh template 400. Since the ellipse shape 404 comprises the pre-located sutures 408, 410, 412, 414, the surgeon may not have to add additional sutures to the ellipse shape 404 while repairing the fascial defect.

Referring now to FIG. 5, illustrated is an example ventral hernia mesh template comprising pre-located sutures. The mesh template can comprise equidistant reference lines in relation to a midpoint according to a shape of the mesh template. Reference lines and reference numerals can be placed circumferentially at defined points measured at a distance from a center of the template. The reference lines can be standard measured lines in numbered increments. For example, reference numerals representing a two centimeter distance can be placed equidistant from the center of the mesh template, reference numerals representing a four centimeter distance can be placed equidistant from the center of the mesh template, etc. Thus, the mesh template can comprise numbers representing distances in relation to the reference lines spaced equidistantly from a midpoint of the mesh template. Furthermore, the mesh template can comprise a perforated shape, wherein the perforated shape is in accordance with the shape of the mesh template The mesh template can comprise perforations at one or more reference lines, which can facilitate one template being able to be utilized for several sized fascial defects. Each perforated shape/design can also be highlighted to provide visibility for each specific shape/design.

The mesh template can comprise a symmetrical shape, wherein similar smaller symmetrical shapes are outlined by perforations. The mesh template can comprise a geometric representation of the fascial defects and references letters or numbers to indicate representative spacing. The reference lines can be standard measured lines in numbered increments representing similar shapes within the mesh template. The mesh template can also comprise perforations at one or more reference lines, which can facilitate one template being able to be utilized for several sized fascial defects. Each perforated shape/design can also be highlighted to provide visibility for each specific shape/design. The mesh template can comprise a label representing a distance associated with the similar smaller symmetrical shapes, and a prong adjacently attached to the mesh template.

The strategic locations of the sutures can form several patterns, including but not limited to: diamond, ellipse, and/or circular type patterns depending on what type of hernia is being repaired. The mesh template 500 can comprise center lines 502 504 with perforated circular shapes 506 508. The mesh template 500 can also comprise pre-located sutures 510, 512, 514, 516. Therefore, if a surgeon uses the mesh template 500 to measure an circular shaped fascial defect, and the size of the fascial defect is close to that of the circular shape 506, then the surgeon can remove the circular shape 506 from the mesh template 500. Since the circular shape 506 comprises the pre-located sutures 510, 512, 514, 516, the surgeon may not need to add additional sutures to the circular shape 506 while repairing the fascial defect.

Referring now to FIG. 6, illustrated is an example system block diagram for a method for using a mesh template apparatus. At element 600, a mesh template can be selected according to a perceived shape of a hernia. The mesh template can be used to help a surgeon to accurately measure a fascial defect and can help the surgeon draw the dimensions of the hernia defect directly onto the mesh to allow the surgeon to shape and cut away excess mesh. At element 602, the mesh template can be aligned with a hernia, and numbers on the mesh template representing distances in relation to the hernia can be identified numbers at element 604. Thus, accurate size identification based on the mesh template can be used to select a mesh based on the perceived shape of the hernia and the identified numbers on the hernia mesh at element 606.

Figure 7:
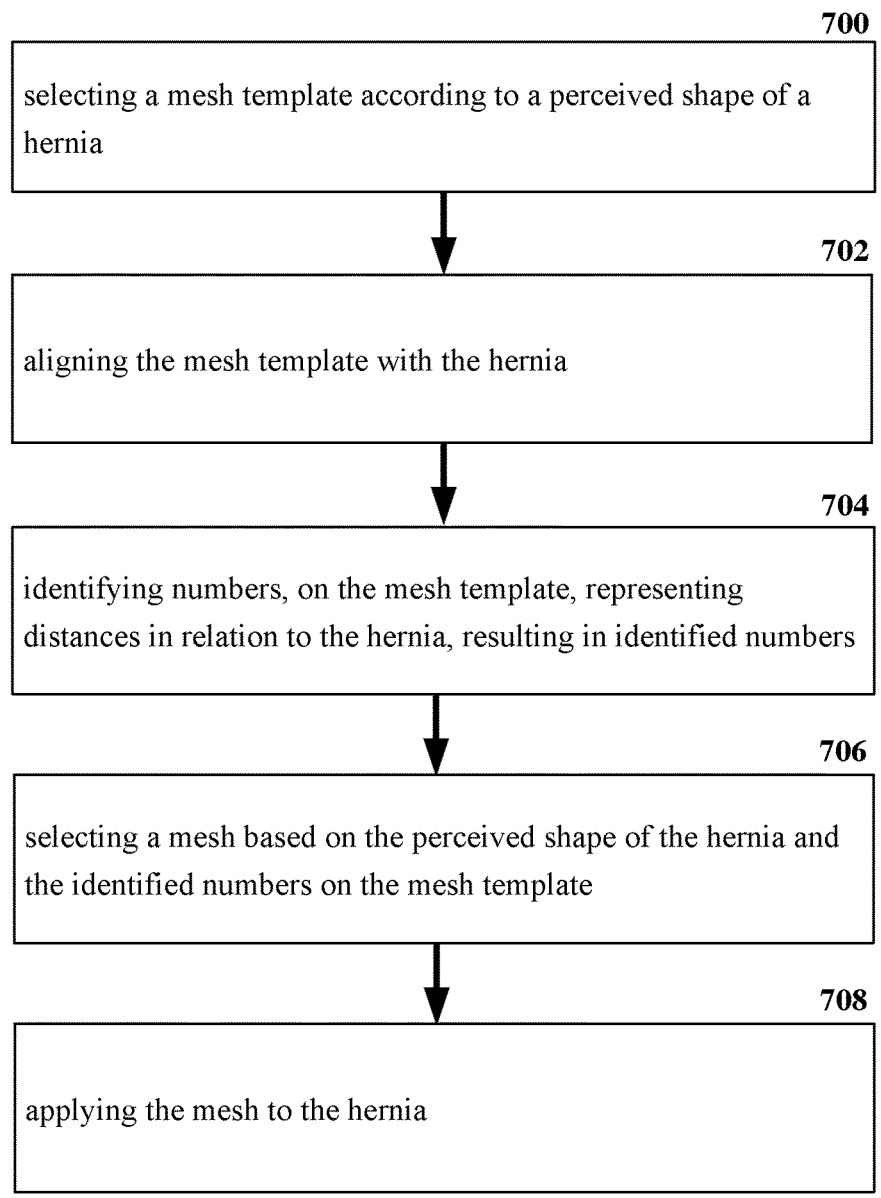
FIG. 7 illustrates is an example system block diagram for a method of using a mesh template apparatus comprising applying the mesh template to the hernia.

Referring now to FIG. 7, illustrated is an example system block diagram for a method for using a mesh template apparatus comprising applying the mesh template to the hernia. At element 700, a mesh template can be selected according to a perceived shape of a hernia. The mesh template can be used to help a surgeon to accurately measure a fascial defect and can help the surgeon draw the dimensions of the hernia defect directly onto the mesh to allow the surgeon to shape and cut away excess mesh. At element 702, the mesh template can be aligned with a hernia, and numbers on the mesh template representing distances in relation to the hernia can be identified numbers at element 704. Thus, accurate size identification based on the mesh template can be used to select a mesh based on the perceived shape of the hernia and the identified numbers on the hernia mesh at element 706. At element 708, the mesh template can be applied to the hernia.

Figure 8:
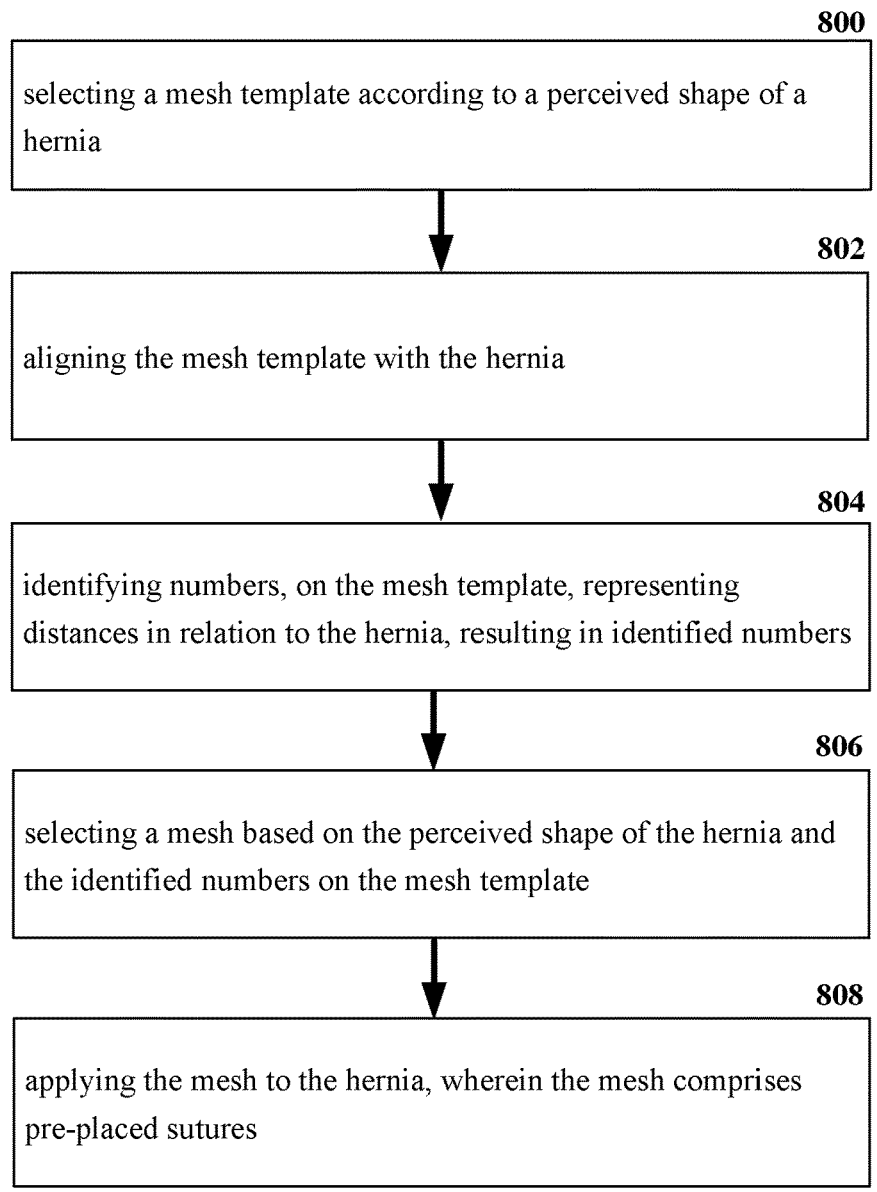
FIG. 8 illustrates is an example system block diagram for a method of using a mesh template apparatus comprising applying the mesh template to the hernia, wherein the mesh comprises pre-placed sutures

Referring now to FIG. 8, illustrated is an example system block diagram for a method for using a mesh template apparatus comprising applying the mesh template to the hernia, wherein the mesh comprises pre-placed sutures. At element 800, a mesh template can be selected according to a perceived shape of a hernia. The mesh template can be used to help a surgeon to accurately measure a fascial defect and can help the surgeon draw the dimensions of the hernia defect directly onto the mesh to allow the surgeon to shape and cut away excess mesh. At element 802, the mesh template can be aligned with a hernia, and numbers on the mesh template representing distances in relation to the hernia can be identified numbers at element 804. Thus, accurate size identification based on the mesh template can be used to select a mesh based on the perceived shape of the hernia and the identified numbers on the hernia mesh at element 806. At element 808, the mesh template can be applied to the hernia, and the mesh template can comprise pre-placed sutures. A mesh-suture combination can have several sutures that have already been strategically placed on the mesh during processing. There can be a complete set of sutures surrounding the entire mesh.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the subject matter has been described herein in connection with various embodiments and corresponding FIGs, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A mesh template apparatus, comprising:
   first equidistant reference lines concentric about a first midpoint according to a first shape of the mesh template on a first side of the mesh template;
   second equidistant reference lines concentric about a second midpoint according to a second shape of the mesh template on a second side of the mesh template, wherein the second shape is different than the first shape;
   numbers representing distances in relation to the first equidistant reference lines and the second equidistant reference lines, wherein the numbers are spaced equidistantly from each other and define increasing distances from the first midpoint or the second midpoint of the mesh template;
   a first perforated shape, formed by the first equidistant reference lines, wherein the first perforated shape is in accordance with the first shape of the mesh template; and
   a second perforated shape, formed by the second equidistant reference lines, wherein the second perforated shape is in accordance with the second shape of the mesh template.

2. The apparatus of claim 1, further comprising:
   a positioning piece, wherein the positioning piece facilitates placement of the mesh template apparatus.

3. The apparatus of claim 1, wherein the first shape of the mesh template comprises a circular shape, and wherein the first side of the mesh template comprises a paper material.

4. The apparatus of claim 3, wherein the first perforated shape is highlighted and the second perforated shape is highlighted.

5. The apparatus of claim 1, wherein the second shape of the mesh template comprises an oval shape, and wherein the second side of the mesh template comprises a plastic material.

6. The apparatus of claim 5, wherein the first perforated shape is highlighted and the second perforated shape is highlight.

7. The apparatus of claim 1, wherein the first perforated shape is highlighted.

8. The apparatus of claim 1, wherein the first or second shape of the mesh template comprises an oval shape.

9. The apparatus of claim 1, wherein the first or second shape of the mesh template comprises a diamond shape.

10. A method, comprising:
    selecting a mesh template according to a perceived shape of a hernia;
    aligning the mesh template with the hernia;
    identifying numbers, on the mesh template, representing distances concentric about the hernia, resulting in identified numbers; and
    based on a first perforated shape on a first side of the mesh template, wherein the first perforated shape is different than a second perforated shape on a second side of the mesh template, using the template to select a mesh based on the perceived shape of the hernia and the identified numbers on the mesh template.

11. The method of claim 10, further comprising:
    applying the mesh to the hernia.

12. The method of claim 11, wherein the mesh comprises pre-placed sutures.

13. The method of claim 12, further comprising:
    stitching the mesh to a fascia surrounding the hernia via the pre-placed sutures.

14. The method of claim 11, further comprising:
    stitching the mesh to the hernia via sutures.

15. The method of claim 10, wherein the mesh comprises biological tissues and synthetic materials.

16. The method of claim 10, wherein the mesh template comprises a positioning piece to facilitate positioning of the mesh template.

17. The method of claim 10, wherein the mesh template comprises silastic and the first perforated shape is that of an oval shape.

18. The method of claim 10, wherein the first side or second side of the mesh template comprises a diamond shape.

19. The method of claim 10, wherein the mesh template comprises tin and the first perforated shape is that of a circular shape.

\* \* \* \* \*